US009764147B2

(12) United States Patent
Torgerson

(10) Patent No.: US 9,764,147 B2
(45) Date of Patent: Sep. 19, 2017

(54) CHARGE-BASED STIMULATION INTENSITY PROGRAMMING WITH PULSE AMPLITUDE AND WIDTH ADJUSTED ACCORDING TO A FUNCTION

(75) Inventor: Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1558 days.

(21) Appl. No.: 12/429,931

(22) Filed: Apr. 24, 2009

(65) Prior Publication Data

US 2010/0274320 A1  Oct. 28, 2010

(51) Int. Cl.
*A61N 1/00* (2006.01)
*A61N 1/372* (2006.01)
*G06F 19/00* (2011.01)
*A61N 1/36* (2006.01)

(52) U.S. Cl.
CPC ....... *A61N 1/37247* (2013.01); *A61N 1/3615* (2013.01); *A61N 1/36167* (2013.01); *G06F 19/3406* (2013.01); *G06F 19/3418* (2013.01); *A61N 1/36082* (2013.01)

(58) Field of Classification Search
CPC .......................... A61N 1/37247; A61N 1/3615
USPC ................... 607/4, 5, 10, 46, 48, 59
See application file for complete search history.

(56) References Cited

U.S. PATENT DOCUMENTS

| | | | |
|---|---|---|---|
| 4,431,002 A | 2/1984 | Maurer et al. | |
| 4,590,941 A | 5/1986 | Saulson et al. | |
| 5,158,078 A | 10/1992 | Bennett et al. | |
| 5,447,525 A | 9/1995 | Powell et al. | |
| 5,480,414 A | 1/1996 | Stroebel et al. | |
| 5,645,573 A | 7/1997 | Kroll et al. | |
| 5,697,956 A | 12/1997 | Bornzin | |
| 6,393,325 B1 | 5/2002 | Mann et al. | |

(Continued)

FOREIGN PATENT DOCUMENTS

| | | |
|---|---|---|
| EP | 0 054 321 | 6/1982 |
| EP | 0524321 | 1/1993 |

(Continued)

OTHER PUBLICATIONS

Invitation to Pay Additional Fees along with Partial Search Report for corresponding PCT Application PCT/US2010/026593 dated Jun. 10, 2010 (5 pgs.).
Notification of Transmittal of the International Search Report and the Written Opinion for corresponding PCT Application PCT/US2010/026593 dated Jul. 27, 2010 (22 pgs.).
U.S. Appl. No. 12/111,822, filed Apr. 29, 2008 by Stone et al., entitled: Configuring Stimulation Therapy Using Stimulation Intensity.

(Continued)

*Primary Examiner* — Nadia A Mahmood
(74) *Attorney, Agent, or Firm* — Shumaker & Sieffert, P.A.

(57) ABSTRACT

Techniques for programming electrical stimulation therapy intensity based on electrical charge are described. In some examples, a display presents a stimulation intensity value in units of electrical charge, e.g., Coulombs. In such examples, a user may adjust the displayed charge value, rather than pulse amplitude or pulse width, to adjust the intensity of the electrical stimulation therapy. In some examples, a processor determines modifications to pulse amplitude and pulse width based on the modification to the charge value. In some examples, a processor modifies a pulse amplitude and width to achieve a desired charge, while maintaining a relationship between pulse amplitude and width specified by a predetermined function. In some examples, the function may be programmed, e.g., selected or adjusted, by a user.

30 Claims, 15 Drawing Sheets

(56) References Cited

U.S. PATENT DOCUMENTS

| | | |
|---|---|---|
| 6,456,879 B1 | 9/2002 | Weinberg |
| 6,516,227 B1 | 2/2003 | Meadows et al. |
| 6,587,724 B2 | 7/2003 | Mann |
| 6,594,523 B1 | 7/2003 | Levine |
| 6,609,032 B1 | 8/2003 | Woods et al. |
| 6,615,082 B1 | 9/2003 | Mandell |
| 6,618,621 B1 | 9/2003 | Holmström |
| 6,622,048 B1 | 9/2003 | Mann et al. |
| 6,738,668 B1 | 5/2004 | Mouchawar et al. |
| 7,050,856 B2 | 5/2006 | Stypulkowski |
| 7,082,333 B1 | 7/2006 | Bauhahn et al. |
| 7,127,296 B2 | 10/2006 | Bradley |
| 7,158,826 B1 | 1/2007 | Kroll et al. |
| 7,174,215 B2 | 2/2007 | Bradley |
| 7,254,444 B2 | 8/2007 | Moore et al. |
| 7,280,868 B2 | 10/2007 | Rueter et al. |
| 7,403,819 B1 | 7/2008 | Shelchuk et al. |
| 2003/0074025 A1* | 4/2003 | Wuthrich ............ 607/5 |
| 2004/0143303 A1 | 7/2004 | Sieracki et al. |
| 2006/0229687 A1 | 10/2006 | Goetz et al. |
| 2007/0055322 A1* | 3/2007 | Forsberg et al. ........... 607/59 |
| 2007/0083104 A1 | 4/2007 | Butson et al. |
| 2007/0288064 A1 | 12/2007 | Butson et al. |
| 2008/0071318 A1 | 3/2008 | Brooke et al. |
| 2008/0103533 A1 | 5/2008 | Patel et al. |
| 2008/0103559 A1* | 5/2008 | Thacker et al. ............ 607/62 |
| 2008/0300644 A1 | 12/2008 | Sathaye |

FOREIGN PATENT DOCUMENTS

| | | |
|---|---|---|
| WO | WO 2004/052451 A1 | 6/2004 |
| WO | WO 2008/121891 A1 | 10/2008 |

OTHER PUBLICATIONS

Volkmann et al., "Introduction to the Programming of Deep Brain Stimulators," Movement Disorders, vol. 17, No. 3, pp. S181-S187 (2002).

Office Action dated Dec. 12, 2011 for U.S. Appl. No. 12/111,822, (8 pgs.).

Responsive Amendment dated Mar. 12, 2012 for U.S. Appl. No. 12/111,822, (11 pgs.).

Office Action from U.S. Appl. No. 12/111,822, dated Sep. 25, 2012, 10 pp.

Response to Office Action dated Sep. 25, 2012, from U.S. Appl. No. 12/111,822, filed Nov. 26, 2012, 13 pp.

Advisory Action from U.S. Appl. No. 12/111,822, dated Dec. 7, 2012, 2 pp.

Supplemental Response to Office Action dated Sep. 25, 2012, from U.S. Appl. No. 12/111,822, filed Jan. 23, 2013, 13 pp.

Chinese Office Action from application No. 201080019008.2, dated Aug. 21, 2013, 11 pp.

Chinese Office Action from Chinese Application No. 201080019008.2, dated Jan. 24, 2014, 4 pp.

* cited by examiner

CHARGE-BASED STIMULATION INTENSITY PROGRAMMING WITH PULSE AMPLITUDE AND WIDTH ADJUSTED ACCORDING TO A FUNCTION

TECHNICAL FIELD

The invention relates to medical systems and, more particularly, medical systems that deliver electrical stimulation therapy.

BACKGROUND

Medical devices have been used to deliver electrical stimulation therapy to patients to treat a variety of symptoms or conditions, such as chronic pain, tremor, Parkinson's disease, epilepsy, urinary or fecal incontinence, and sexual dysfunction. The electrical stimulation is generally delivered to selected target tissues or locations in a patient's body, such as the brain, the spinal cord, pelvic nerves, or peripheral nerves. Hence, stimulation is used in different therapeutic applications, such as spinal cord stimulation (SCS), deep brain stimulation (DBS), pelvic stimulation, or peripheral nerve stimulation. Medical devices have also been used to deliver electrical stimulation to the heart, e.g., for cardiac pacing, and muscles, e.g., for functional electrical stimulation (FES) to promote muscle movement or prevent atrophy.

Such medical devices typically deliver electrical stimulation therapy in the form of electrical pulses. In many examples, the medical devices that deliver stimulation have been implantable. Implantable medical devices typically deliver electrical stimulation via one or more leads that include electrodes located proximate to target tissues. Implantable medical devices are often able to be communicated with and programmed using an external computing device—referred to a programming device or programmer—that wirelessly and transcutaneously communicates with the implantable medical device.

In most cases, a clinician selects values for a number of programmable parameters in order to define the electrical stimulation therapy to be delivered by the implantable stimulator to a patient. For example, a clinician may select an amplitude value, which may be a current or voltage amplitude, and a pulse width value for a stimulation waveform of the electrical stimulation therapy to be delivered to the patient. In addition, the clinician may also select a pulse rate or frequency for stimulation pulses to be delivered to the patient, a combination of electrodes carried by one or more implantable leads to deliver the stimulation, and the polarities of the selected electrodes. A group of parameters, which can include amplitude, pulse width, pulse frequency, electrode combination and electrode polarity, may be referred to as a program in the sense that they drive the electrical stimulation therapy to be delivered to the patient.

In most cases, a clinician creates the one or more programs that a medical device will use to deliver therapy to a patient during an initial programming session. In the case of implantable medical devices, the initial programming session typically occurs shortly after the device is implanted in the patient. The values for each of the parameters of a program may have a significant impact on the efficacy and side effects of the delivery of therapy according to that program. The process of selecting values for the parameters that provide adequate results can be time consuming. In particular, the process may require a great deal of trial-and-error testing of numerous potential combinations of parameter values before a "best" program is discovered. For example, a "best" program may be a program that is better in terms of clinic efficacy versus side effects experienced than other programs tested. As another example, a best program may also be a program that requires relatively less energy than other programs, such that energy consumed by the electrical stimulation is minimized and power source longevity of the medical device is maximized.

In some cases, the clinician may need to test a large number of possible electrode configurations, i.e., combinations and polarities, in order to identify a desirable configuration. During the testing of an electrode configuration, the clinician may select a pulse width, and then adjust amplitude to identify one or more amplitude thresholds, such as the amplitude at which stimulation is first perceived by the patient (or perception threshold), and the maximum amplitude at which stimulation is still comfortable or the amplitude at which side effects from stimulation become intolerable. A usage range, e.g., a range of amplitudes useable for stimulation therapy, may be defined based on these amplitude thresholds. Additionally or alternatively, the clinician may identify a usage amplitude, which may be an amplitude at which stimulation is effective and results in minimal, tolerable, or no side effects. The clinician may select the pulse-width based on intuition or experience. The clinician may repeat the time-consuming amplitude adjustment process for the electrode configuration with one or more other fixed pulse widths, or may proceed to another electrode configuration after having tested only one pulse width.

Even after this often-lengthy process, the programs selected during an initial programming session may ultimately prove to be inadequate. The eventual inadequacy of the initial programming may be due to a variety of problems, including progression of symptoms and/or an underlying ailment, increased or changed symptoms or side effects during activities and/or postures that were not replicated in the clinic during the initial programming session, slow onset of side effects and, in the case of delivery of stimulation via electrodes located on implantable leads, lead migration. An example of a therapy for which side effects and efficacy are generally not apparent until a program has been applied for an extended period of time is deep brain stimulation.

Patients have been given the ability to adjust stimulation outside of the clinic, at least in part to address such situations. For example, patients with implantable medical devices have been provided an external programming device, referred to as a patient programmer or patient therapy manager, that is simplified relative to the programming device used by a clinician. The patient may use the patient programmer to adjust the stimulation, although often in a manner that is restricted relative to the clinician. In practice, patients often adjust pulse amplitude, without adjusting pulse width, to achieve a desired change in the efficacy or side effects of stimulation.

SUMMARY

Only or primarily modifying amplitude as a means to adjust stimulation intensity, as has been done by both clinicians and patients, may not identify more desirable combinations of pulse amplitude and pulse width for the stimulation. Longer pulse width values may be more efficient in the sense that they may facilitate efficacious stimulation that consumes less power from a power source of a medical device. Longer pulse width values may also provide more comfortable stimulation, e.g., with fewer undesired sensations or other side effects. Longer pulse width values may additionally enable the overall intensity of stimulation to be greater as amplitude is adjusted.

In general, the disclosure is directed to techniques for programming electrical stimulation therapy intensity based on electrical charge. In some examples, a display presents a stimulation intensity value in units of electrical charge, e.g., nanoCoulombs. In such examples, a user may adjust the displayed charge value, rather than pulse amplitude or pulse width, to adjust the intensity of the electrical stimulation therapy.

A processor determines modifications to pulse amplitude and pulse width based on user input controlling the charge of the stimulation, such as user modification of a displayed charge value. In particular, the processor modifies the pulse amplitude and width to achieve the desired amount of charge according to a predetermined function relating pulse amplitude to pulse width. In some examples, the function may be programmed, e.g., selected or adjusted, by a user. The function may be selected, for example, to promote power consumption efficiency or comfort of the stimulation. Programming electrical stimulation therapy intensity based on a single parameter, i.e., electrical charge, rather than multiple parameters, may increase the speed of programming, i.e., finding a desirable combination of pulse amplitude and width.

In one example, a method comprises storing a predetermined function specifying a relationship between pulse amplitude and pulse width within a memory, receiving input from a user modifying an electrical charge value of neurostimulation delivered by a medical device, and modifying a pulse amplitude and a pulse width of the neurostimulation delivered by the medical device according to the function and based on the modification of the charge value.

In another example, a system comprises a memory that stores a predetermined function specifying a relationship between pulse amplitude and pulse width, a medical device that delivers neurostimulation to a patient, a user interface that receives input from a user modifying an electrical charge value of neurostimulation delivered by a medical device, and a processor. The processor communicates with the memory, medical device and user interface, and modifies a pulse amplitude and a pulse width of the neurostimulation delivered by the medical device according to the function and based on the modification of the charge value.

In another example, a system comprises means for storing a predetermined function specifying a relationship between pulse amplitude and pulse width, means for receiving input from a user modifying an electrical charge value of neurostimulation delivered by a medical device, and means for modifying a pulse amplitude and a pulse width of the neurostimulation delivered by the medical device according to the function and based on the modification of the charge value.

In another example, a computer-readable storage medium comprises instructions that cause a programmable processor to retrieve a predetermined function specifying a relationship between pulse amplitude and pulse width from a memory, receive input from a user modifying an electrical charge value of neurostimulation delivered by a medical device, and modify a pulse amplitude and a pulse width of the neurostimulation delivered by the medical device according to the function and based on the modification of the charge value.

In another example, a method comprises storing a predetermined function specifying a relationship between pulse amplitude and pulse width within a memory, receiving user-inputted modifications to one of a pulse amplitude or a pulse width of neurostimulation delivered from a medical device to a patient, determining a modification to both of the pulse amplitude and the pulse width according to the function with equivalent intensity to the user-inputted modification to the one of the pulse amplitude or pulse width, and modifying the pulse amplitude and pulse width of the stimulation according to the determination.

DETAILED DESCRIPTION

Figure 1:
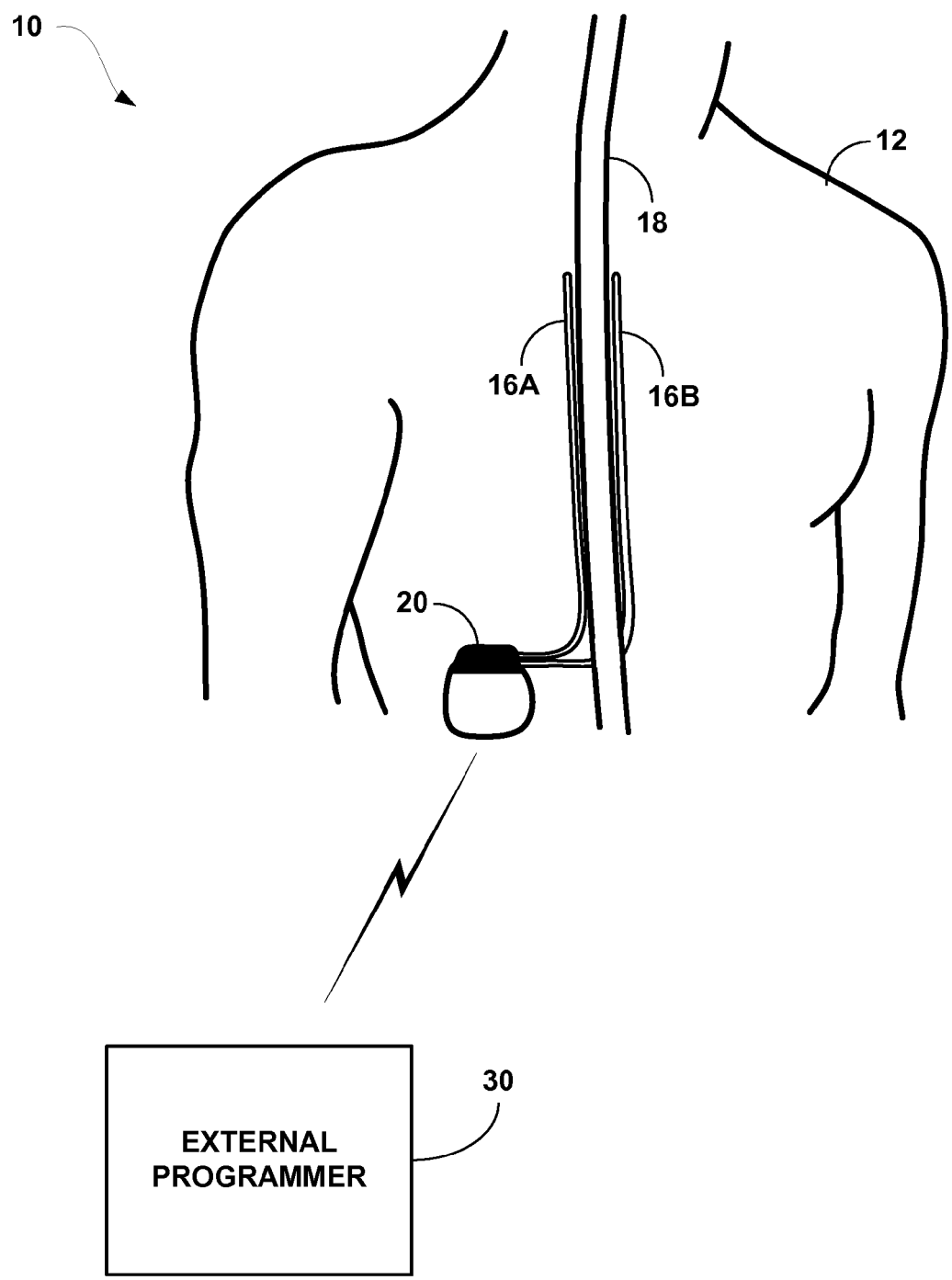
FIG. 1 is a conceptual diagram illustrating an example stimulation therapy system.

FIG. 1 is a conceptual diagram illustrating an example stimulation therapy system 10 that delivers therapeutic electrical stimulation to patient 12. Therapy system 10 includes an implantable medical device (IMD) 20, which is coupled to leads 16A and 16B (collectively "leads 16"), and communicates with an external programmer 30. Leads 16 each include one or more electrodes (not shown in FIG. 1). IMD 20 delivers electrical stimulation to patient 12 via the electrodes. The illustrated number and location of leads is merely one example. Furthermore, the techniques described herein may be practiced by systems in which the medical device and/or leads are not implantable, or which do not include leads and/or a programmer.

In the illustrated example, IMD 20 delivers spinal cord stimulation (SCS) to the spinal cord 18 of patient 12 to, for example, treat chronic pain. In other examples, an IMD or other medical device delivers deep brain stimulation (DBS), cortical stimulation (CS), peripheral nerve stimulation (PNS), pelvic floor stimulation, gastric stimulation, or peripheral nerve field stimulation (PNFS). Stimulation may be configured to support therapy for a variety of symptoms, diseases and disorders, such as chronic pain, temporary pain, urinary incontinence, fecal incontinence, sexual dysfunction, gastroparesis, obesity, movement disorders, epilepsy, depression, anxiety, or the like. Thus, the techniques for stimulation intensity programming are described with respect to system 10 and SCS, but without limitation as to application of such techniques to other systems, target stimulation sites, or therapy applications.

A user, such as a clinician or patient, interacts with programmer 30 to configure the electrical stimulation delivered by IMD 20. In this manner, programmer 30 controls the stimulation delivered by IMD 20. In various examples, programmer 30 comprises a handheld device, portable computer, or workstation that provides a user interface to a clinician. Programmer 30 communicates with IMD 20 using any medical device telemetry or other wireless communication techniques known in the art. In some examples, programmer 30 is a remote device that communicates with IMD 20 via a network. Programmer 30 may be a relatively full-featured clinician programmer, or a patient programmer with relatively limited control over the operation of IMD 20.

The clinician interacts with programmer 30 to program stimulation parameters, such as pulse amplitude, width and rate, as well as to select a configuration of the electrodes on leads 16 through which the stimulation is delivered. Different combinations of values for such stimulation parameters may be referred to as a program. IMD 20 delivers stimulation therapy according to one or more programs.

System 10 is one example of a system that facilitates programming the intensity of the electrical stimulation therapy based on electrical charge. Using programmer 30, a user may adjust an electrical charge value, rather than pulse amplitude or pulse width, to adjust the intensity of the electrical stimulation therapy. A processor within one or both of IMD 20 or programmer 30 may determine modifications to pulse amplitude and pulse width based on the modification to the charge value. In particular, the processor modifies the pulse amplitude and width to achieve the desired charge by adjusting the pulse amplitude and width according to a predetermined function relating pulse amplitude and width, which may be stored within one or both of IMD 20 and programmer 30. In some examples, the user may select or adjust the function relating pulse amplitude and pulse width using programmer 30.

Figure 2:
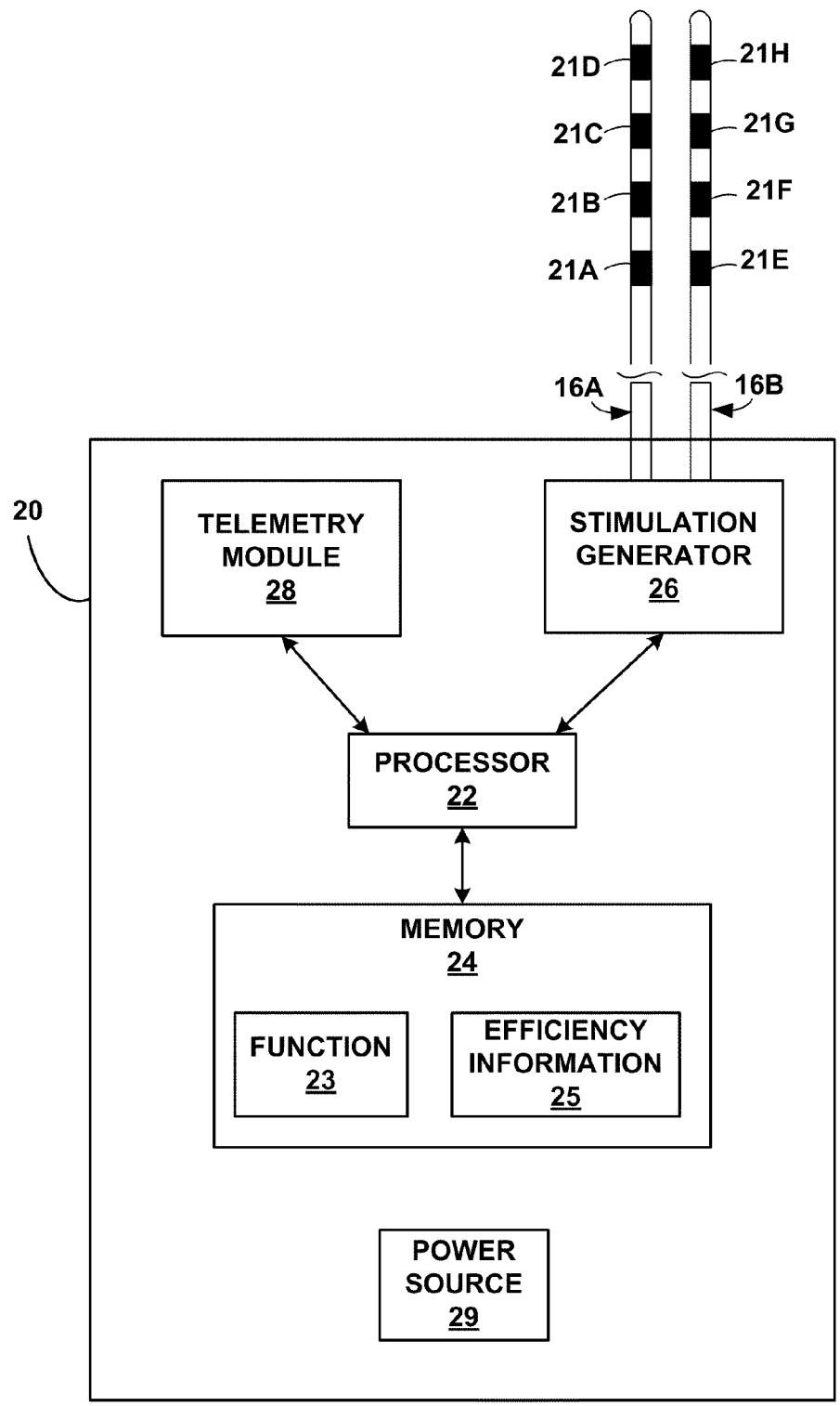
FIG. 2 is a block diagram illustrating an example configuration of an implantable medical device that delivers electrical stimulation therapy.

FIG. 2 is a block diagram illustrating an example configuration of IMD 20. In the example of FIG. 2, IMD 20 includes a processor 22, memory 24, stimulation generator 26, telemetry module 28 and power source 29. As shown in FIG. 2, stimulation generator 26 is coupled to leads 16. Each of leads 16A and 16 respectively comprises electrodes 21A-21D and 21E-21H (collectively "electrodes 21").

Processor 22 controls stimulation generator 26 to deliver electrical stimulation therapy according to stimulation parameters, e.g., programs, stored in memory 24 and/or received from programmer 30 via telemetry module 28. In some cases, stimulation parameter values received from programmer 30 are in fact commands to modify, e.g., increment or decrement, one or more stimulation parameter values, such as pulse width or pulse amplitude. Stimulation generator 26 provides stimulation to electrodes 21 in the form of pulses. Stimulation generator 26 may utilize, under the control of processor 22, any combination or configuration of electrodes 21 on leads 16.

Processor 22 may comprise any one or more of a microprocessor, digital signal processor (DSP), application specific integrated circuit (ASIC), field-programmable gate array (FPGA), or other digital logic circuitry. Memory 24 stores instructions for execution by processor 22 e.g., instructions that when executed by processor 22 cause the processor and IMD 20 to provide the functionality ascribed to them herein. Memory 72 may include any one or more of a random access memory (RAM), read-only memory (ROM), electronically-erasable programmable ROM (EEPROM), flash memory, or the like. The functions attributed to processor 22 herein may be embodied as hardware, firmware, software, or the like.

Telemetry module 28 may include circuitry known in the art for facilitating wireless telemetry, e.g., via radio frequency (RF) communication or proximal inductive interaction with similar circuitry within external programmer 30. Power source 29 delivers operating power to the components of IMD 20. Power source 29 may include a battery and a power generation circuit to produce the operating power. In some embodiments, the battery may be rechargeable to allow extended operation. Recharging may be accomplished through proximal inductive interaction between an external charger and an inductive charging coil within IMD 20. In other embodiments, non-rechargeable batteries may be used. As a further alternative, an external power supply could transcutaneously power IMD 20 whenever stimulation is needed or desired.

In the illustrated example, memory 24 stores a predetermined function 23 relating pulse amplitude to pulse width. In some examples, processor 22 controls stimulation generator 26 to adjust the pulse amplitude and pulse width of the stimulation pulses delivered by the generator according to the function, i.e., in order to maintain or substantially maintain the relationship between the pulse amplitude and width defined by the function 23. Processor 22 may adjust the pulse amplitude and/or width in this manner in response to commands to modify, e.g., increment or decrement, stimulation intensity from programmer 30 received via telemetry module 28, or based on instructions to modify stimulation intensity stored in memory 24, e.g., at a time or after an interval according to a schedule, or in response to some condition sensed via electrodes 21 or another sensor (not shown). Processor 22 may control stimulation generator 26 to increase or decrease both amplitude and pulse width at substantially the same time to maintain the relationship, or may alternate between adjustments to pulse amplitude and width to substantially maintain the relationship.

In the illustrated example, memory 24 also stores efficiency information 25. Efficiency information 25 comprises information regarding the efficiency of various pulse width and/or pulse amplitude values with respect to the requirements of power source 29 for delivery of stimulation with those values. For example, efficiency information 25 may identify pulse amplitude values at which the voltage of power source will need to be multiplied or boosted in order to provide sufficient headroom for stimulation generator 26 to deliver a pulse at that amplitude.

Pulse amplitudes at or just above such a boost value may be inefficient, e.g., a ratio between the amplitude of the pulse and the amount of power required from power source 29 may be relatively low. Efficiency information 25 may identify such amplitudes. These boost amplitudes may change over time as a function of the voltage level of power source 29. Processor 22 may periodically determine a current voltage level of power source 29 and update efficiency information 25. As will be described below, processor 22 may automatically adjust function 23 based on efficiency information 25, e.g., identifying that the stimulation amplitude is approaching a boost point.

Figure 3:
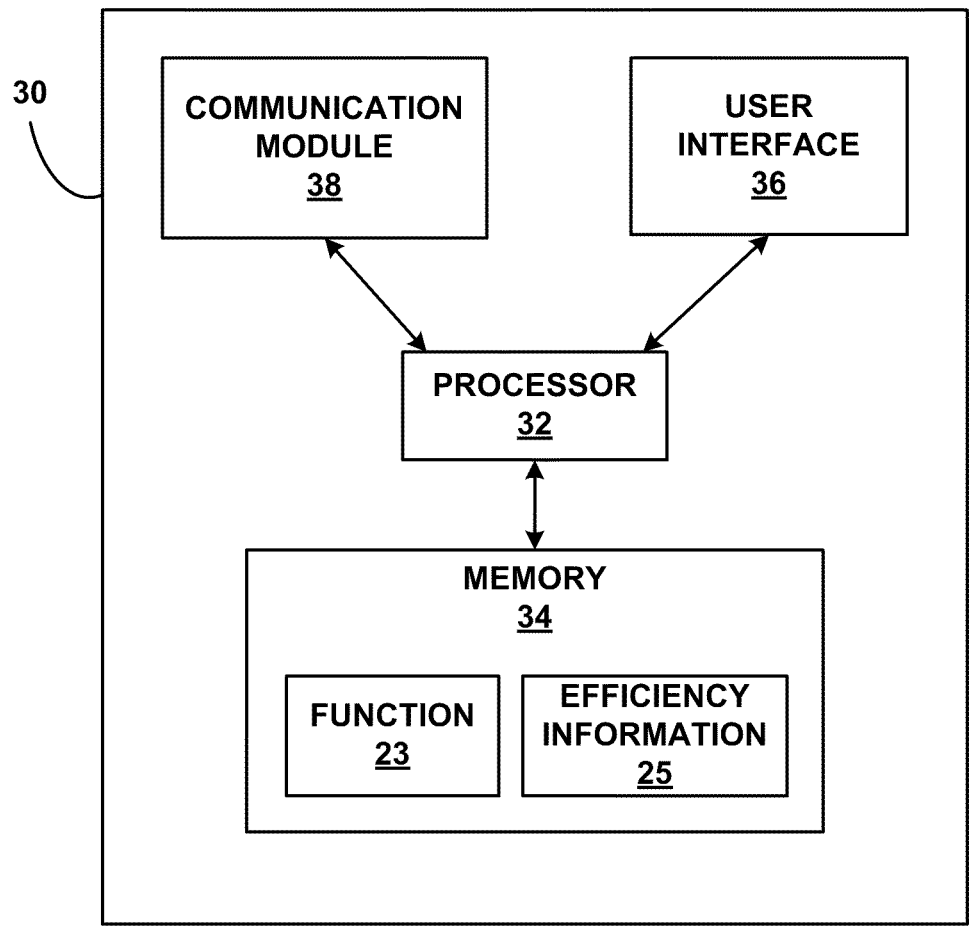
FIG. 3 is a block diagram illustrating an example configuration of an external programming device for programming and controlling the implantable medical device of FIG. 2.

FIG. 3 is a functional block diagram of an example configuration of programmer 30. In the example of FIG. 3, external programmer 30 includes a processor 32, memory 34, user interface 36, and communication module 38. Processor 32 processes instructions from memory 34 and controls the various components of programmer 30 to provide the functionality ascribed to the programmer herein. Processor 32 may comprise any one or more of a microprocessor, digital signal processor (DSP), application specific integrated circuit (ASIC), field-programmable gate array (FPGA), or other digital logic circuitry. The functions ascribed to processor 32 herein may be embodied as hardware, firmware, software, or any combination thereof. Memory 34 stores the instructions executed by processor 32. Memory 34 may include any one or more of a random access memory (RAM), read-only memory (ROM), electronically-erasable programmable ROM (EEPROM), flash memory, or the like.

A user, either a clinician or patient 12, may interact with processor 32 through user interface 36. Any of the user interfaces described herein may be an example of or provided by user interface 36, such as graphical user interfaces 70 and 90 of FIGS. 8 and 9. User interface 36 may include a display, such as a liquid crystal display (LCD), light-emitting diode (LED) display, or other screen, to show information related to stimulation therapy, and buttons or a pad to provide input to programmer 30. User interface 36 may also comprise input media such as buttons, soft keys, a pointing device, i.e. a mouse, a trackball, a scroll wheel, a pointstick, or a touchpad. In some embodiments, the display may be a touch screen that enables the user to select options directly from the display screen, e.g., with a stylus.

Wireless telemetry with IMD 20 by programmer 30 may be accomplished by radio frequency (RF) communication or proximal inductive interaction. This wireless communication is possible through the use of communication module 38. Accordingly, communication module 38 may include circuitry known in the art for such communication. In some examples, communication module 38 further comprises a wired or wireless network interface for communication with a computer network, e.g., with a server or database, for transmitting data and/or receiving commands.

In the illustrated example, memory 34 stores predetermined pulse amplitude and pulse width function 23, as well as efficiency information 25 relating to the efficiency of stimulation parameters with respect to use of power source 29 of IMD 20. Function 23 may be programmable via programming device 30. In some examples, a user may modify or select function 23 by communicating with processor 32 via user interface 36. Function 23 may take the form of a numerical ratio which may be applied to one of pulse amplitude or width to determine the other, or an equation including such a ratio and possibly constants or offsets. In some examples, function 23 may take the form of an equation that defines a nonlinear relationship between pulse amplitude and pulse width. In some examples, function 23 may take the form of a plurality of paired pulse amplitude values that meet or substantially meet or satisfy such a ratio or equation, which may be stored in a table or list.

Processor 32 may receive efficiency information 25 from IMD 20 via communication module 38, and store the efficiency information in memory 25. In other examples, memory 34 may be programmed or loaded, during manufacture or at some other time, with efficiency information 25 for IMD 20. Processor 32 may periodically receive voltage levels or other metrics of power source 29 from IMD 20, and update efficiency information based on the voltage levels or other metrics. As will be described in greater detail below, processor 32 may automatically adjust function 23 based on efficiency information 25, e.g., identifying that the stimulation amplitude is approaching a boost point.

In some examples, user interface 36 displays a value of electrical charge, e.g., in nanoCoulombs, representing the intensity of the electrical stimulation delivered from IMD 20 to patient 12. In some examples, user interface 36 receives user-inputted modifications to the charge value to adjust stimulation intensity. Processor 32 provides commands to control IMD 20 to modify the intensity of stimulation via communication module 38 in response to the user-inputted modifications, or in response to programming, e.g., a schedule, stored in memory 34.

In some examples, the commands represent the change in the charge value, or an indication to increment or decrement the charge or stimulation intensity. In such examples, IMD 20 may modify pulse amplitude and pulse width based on the command and in accordance with function 23 stored in its memory 24. In other examples, processor 32 determines modifications to pulse width and amplitude that are in accordance with function 23 stored in memory 34 based on the charge modifications, and transmits the determined modifications to pulse amplitude and width to IMD 20 via communication module 38.

Figure 4:
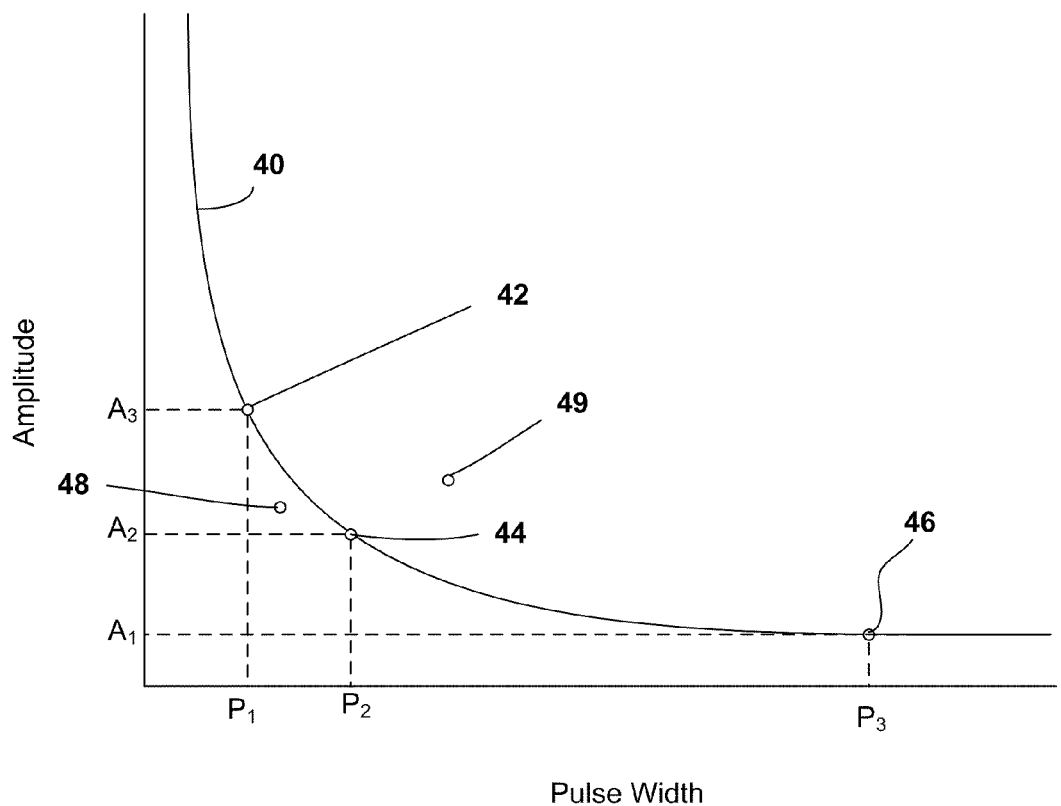
FIG. 4 is diagram illustrating an example strength-duration curve.

FIG. 4 is diagram illustrating an example strength-duration curve 40. Generally, all points along curve 40 define paired pulse width and amplitude values that have substantially equal intensity in the sense that they have a substantially equal ability to activate target neural tissue. For example, a stimulation pulse having a pulse width of $P_1$ and an amplitude of $A_3$, i.e., point 42 on curve 40, a stimulation pulse having a pulse width of $P_2$ and an amplitude of $A_2$, i.e., point 44, and a stimulation pulse having a pulse width of $P_3$ and an amplitude of $A_1$, i.e., point 46, may have substantially equal intensity and a substantially equal ability to capture target neural tissue. In this manner, points 42, 44, 46 define three pulse width and amplitude value pairs, i.e., paired pulse width and amplitude values, which may correspond to a single stimulation intensity.

Curve 40 may be a strength-duration curve specific to target neural tissue. Stimulation pulses with pulse amplitude and width pairs along curve, e.g., at points 42, 44 and 46, may have just sufficient intensity to activate the target neural tissue. Stimulation pulses with pulse amplitude and width pairs above the curve, e.g., with the pair defined by point 49, also activate the target tissue. Stimulation pulses with pulse amplitude and width pairs below the curve, e.g., with the pair defined by point 48, will be of insufficient intensity to activate the target tissue. Curve 40 may be empirically determined for the target neural tissue.

As illustrated by curve 40, there may be a minimum pulse width that is required to activate a target tissue. In general, if a stimulation pulse has a pulse width that is less than this minimum pulse width, the stimulation pulse will likely by unable to activate the tissue no matter how much the amplitude is increased. Similarly, there may be a minimum amplitude along curve 40 that is required to activate a volume of tissue. In some cases, this minimum amplitude may be known as the rheobase amplitude. Additionally, the pulse width value corresponding on curve 40 to twice the rheobase amplitude may be known as the chronaxie.

Although all points on curve 40, including 42, 44 and 46, define individual pulse width and amplitude value pairs providing substantially equal stimulation intensity, the individual paired pulse width and amplitude values are not necessarily substantially equal in all other aspects. For example, stimulation efficiency can vary depending on the pulse width and amplitude value of the stimulation. A pulse with a relatively higher amplitude and lower pulse width, e.g., point 42 relative to point 44, may require boosting of the power source voltage, reducing the efficiency, but may provide effective stimulation with a lower charge density. Alternatively, a pulse with a relatively lower amplitude and higher pulse width may be more efficient with regard to consumption of the energy by the device, e.g., IMD 20, but delivers a pulse with a higher charge density, which may not be desired at higher threshold settings.

Figure 5:
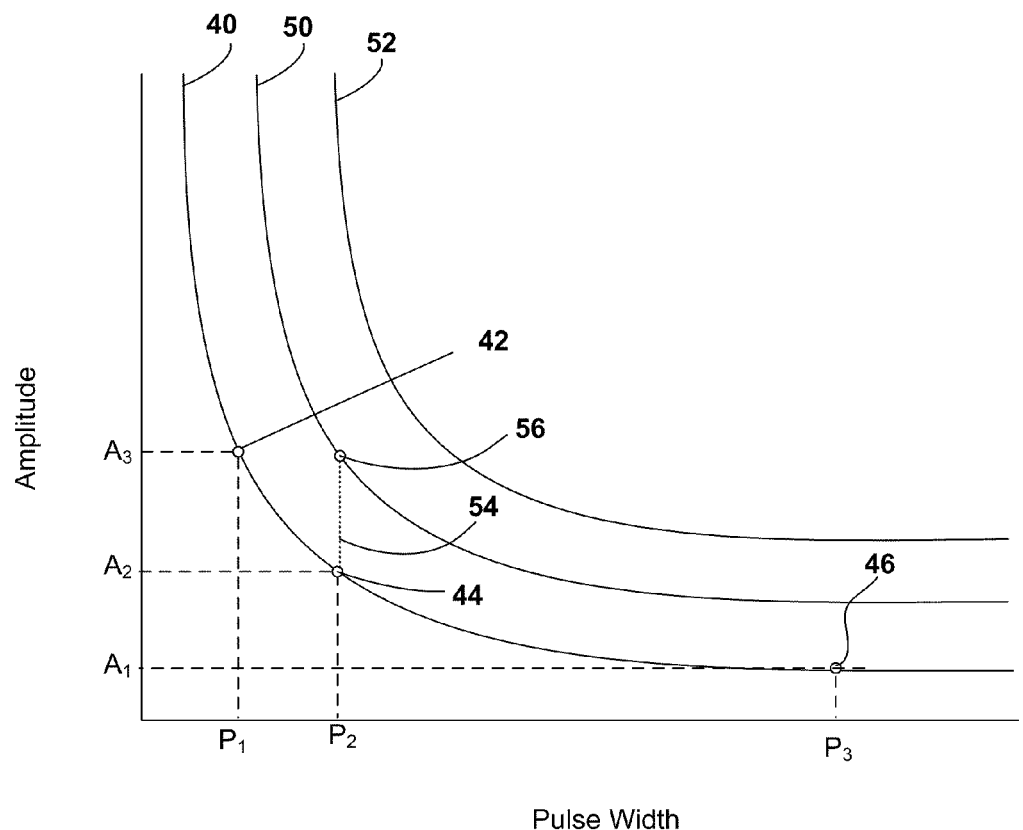
FIG. 5 is a diagram illustrating a plurality of example strength duration curves.

FIG. 5 is a diagram illustrating a plurality of strength-duration curves, including curve 40 from FIG. 4, and curves 50 and 52. Curves 50 and 52 may represent changing of the strength-duration curve for a target neural tissue from curve 40 over time. The changes may occur due to movement of electrodes 21 relative to the target tissue, or changes in the characteristics of the target tissue.

As can be seen in FIG. 5, stimulation pulses with a pulse amplitude and width defined by a point along curve 40, e.g., the amplitude/width pair defined by point 44, will no longer activate the target tissue as the actual strength-duration curve becomes curve 50 or 52. Thus, the stimulation may become ineffective at providing therapeutic benefit. In response to ineffective stimulation, a user, such as a clinician or patient 12, would likely increase the intensity of the stimulation. Traditionally, the user would increase amplitude from a point on curve 40, e.g., A2 at point 44, to increase the intensity. The user would often increase amplitude until the therapeutic effect, e.g., paresthesia, was again perceived. The increasing amplitude is represented by line 54, and the effect would be perceived when, as an example, pulse amplitude reached A3, i.e., point 56 on curve 50. Increasing intensity in this manner changes the ratio between pulse amplitude and pulse width, which may provide less desirable stimulation in terms of power efficiency or comfort, as examples.

Figure 6A:
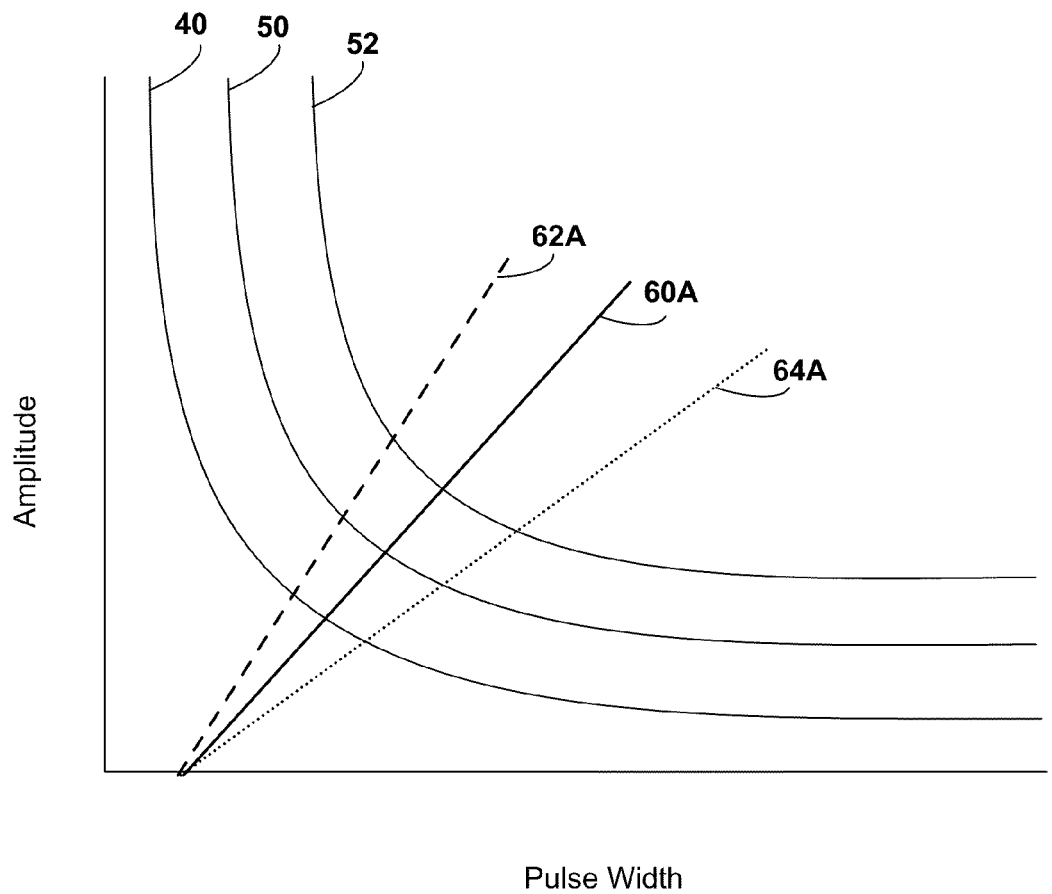
FIGS. 6A and 6B are diagrams illustrating a plurality of lines that represent respective pulse amplitude and pulse width functions intersecting a plurality of strength duration curves.
Figure 6B:
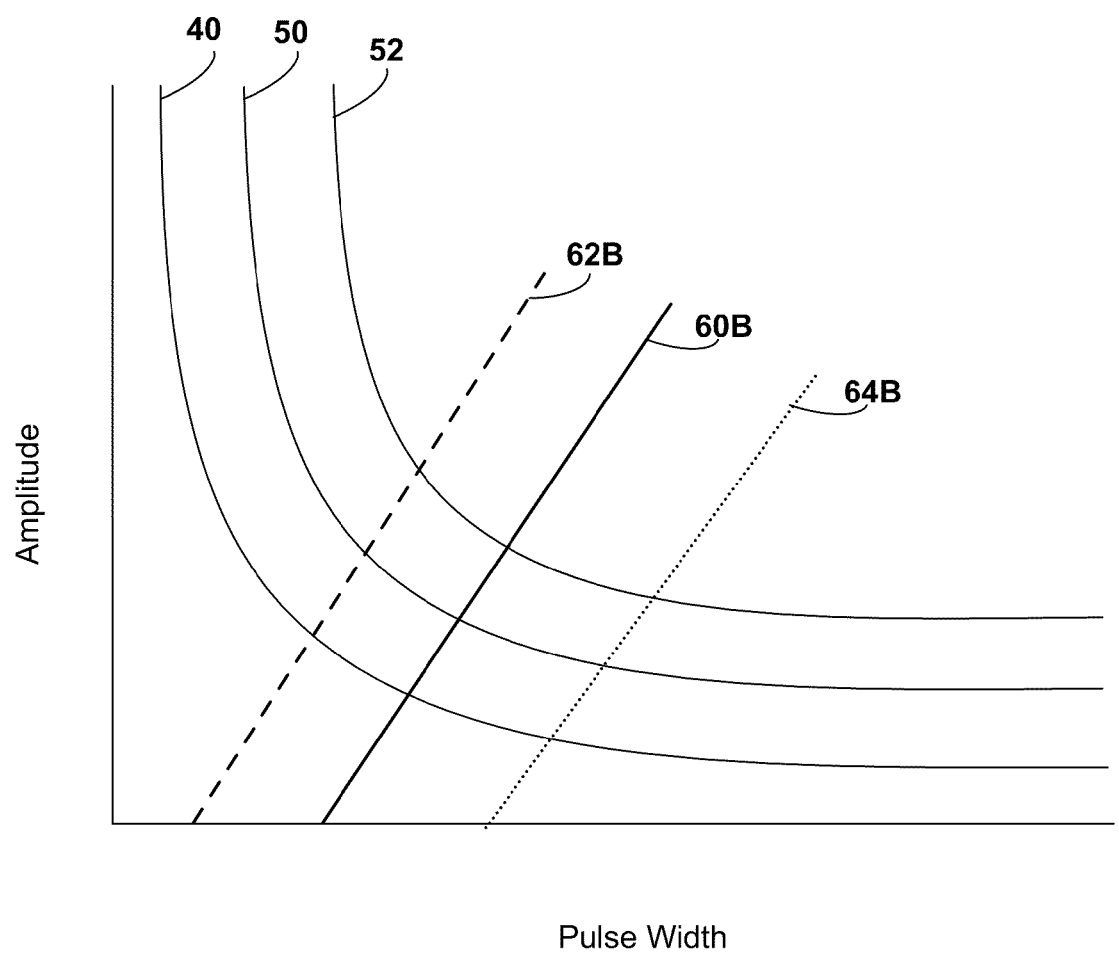

FIGS. 6A and 6B are diagrams illustrating a plurality of lines that represent respective example pulse amplitude and pulse width functions 23 intersecting the plurality of strength-duration curves 40, 50 and 52 of FIG. 5. In particular, lines 60A, 62A and 64A in FIG. 6A, and lines 60B, 62B and 64B in FIG. 6B, represent respective example pulse amplitude and pulse width functions 23 intersecting the plurality of strength-duration curves 40, 50 and 52 of FIG. 5. Lines 60A, 60B, 62A, 62B, 64A and 64B represent pulse amplitude and width pairs that provide increasing stimulation intensity from the origins of the lines. IMD 20 and/or programmer 30 may modify the intensity of stimulation delivered by IMD 20 by titrating along such a line.

The origin of lines 60A, 60B, 62A, 62B, 64A and 64B may be a nonzero pulse width with zero pulse amplitude, as shown in FIGS. 6A and 6B, although other origins are contemplated. Very low pulse widths may activate neural tissue associated with discomfort, and the origin may be selected to avoid such activation. In some examples, the origin for a function 23 is approximately the chronaxie for a typical strength-duration curve for the neural tissue that is the target of the stimulation delivered by IMD 20. As illustrated by FIGS. 6A and 6B, different functions 23 are not limited to a common slope or origin. In other words, various functions 23 may have the same or different slopes, and the same or different origins.

The functions 23 illustrated by lines 60A, 60B, 62A, 62B, 64A and 64B may be fixed or linear ratios between pulse amplitude and pulse width. The functions 23 illustrated by lines 60A, 60B, 62A, 62B, 64A and 64B may be represented by an equation, such as $$PW = b*PA + c \qquad \text{(Equation 1)}$$

where PW is the pulse width, PA is the pulse amplitude, b is the slope of the line, and c is origin (in this case a pulse width value). In some examples, function 23 may take the form of a table or other data structure storing a plurality of pulse amplitude and pulse width pairs that conform to, i.e., meet, such an equation. Furthermore, although the functions illustrated in FIGS. 6A and 6B are fixed or linear ratios between pulse amplitude and pulse width, in other examples a function 23 may take the form of a non-linear, e.g., curvilinear, relationship between pulse amplitude and width.

Figure 7:
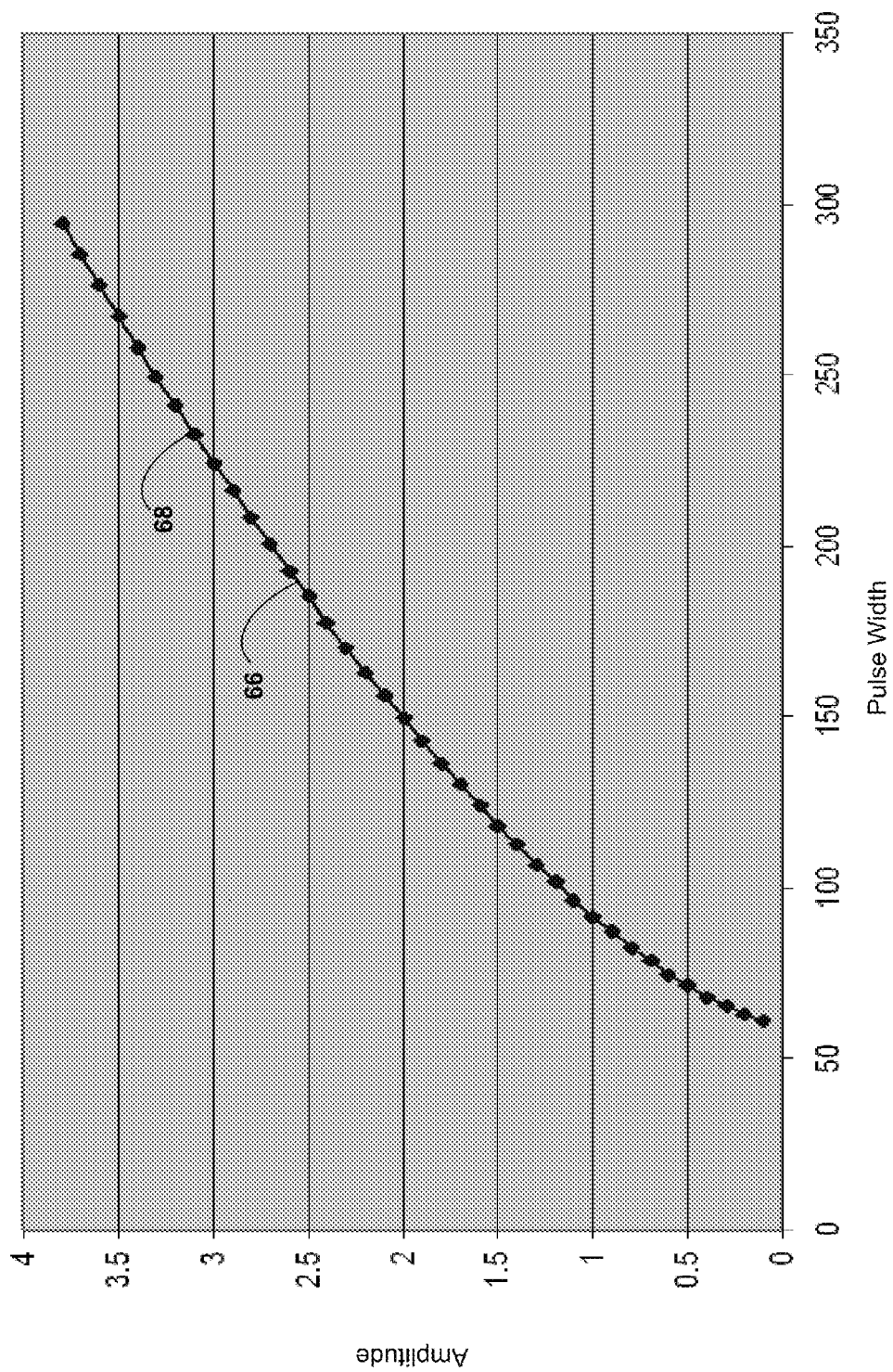
FIG. 7 is a diagram illustrating another example of a pulse amplitude and pulse width function.

FIG. 7 is a diagram illustrating another example pulse amplitude and pulse width function 23. More particularly FIG. 7 illustrates a curve 66 that represents a nonlinear, and more particularly curvilinear, function 23 relating pulse amplitude to pulse width. The function 23 illustrated by curve 66 may be represented by an equation, such as $$PW = (b*\text{Amp})^n + c \qquad \text{(Equation 2)}.$$

Function 23 may define a parabolic, exponential, or logarithmic relationship between pulse amplitude and width, as examples. The points 68 illustrated on curve 66 in FIG. 7, of which only one is labeled, may correspond to pulse amplitude and pulse width pairs stored in a table or other data structure as a function 23.

A function 23 can be selected based on a variety of criteria. In some examples, such as those illustrated by the intersection of lines 60A, 60B, 62A, and 64A with strength-duration curves 40, 50 and 52, function 23 is selected to maintain the stimulation at the "knee" of the typical strength-duration curve for target neural tissue. In some examples, function 23 is chosen based on power efficiency or comfort, e.g., a lower ratio between amplitude and width may be chosen.

In some examples, a user, e.g., clinician, may select or adjust function 23. In such examples, user interface 36 of programmer 30 (FIG. 3) provides input media for such selections or adjustments, or otherwise facilitates such adjustments. In some examples, user interface 36 provides media for entering a numerical value, selecting a numerical value, e.g., from a drop-down list or using a scroll-wheel, or selecting from among functions identified by their characteristics, e.g., "longer pulse width" or "more efficient." In some examples, selecting numerical values may include selecting values for the variables b, c and n in equations 1 and 2 above. In some examples, user interface 36 presents a plurality of equations representing functions 23 to a user for selection.

In some examples, user interface 36 displays a line 60, 62 or 64, or curve 66 representing function 23 so that the user may visualize the function, and may also present one or more curves 40, 50 and 52. In some examples, user interface 36 displays a plurality of lines or curves representing functions 23 for selection of one of the functions 23 by the user by selecting one of the lines or curves. In some examples, user interface 36 provides input media that enables the user to adjust function 23 by adjusting the displayed line or curve, e.g., by clicking on the line or curve and dragging it or changing its shape using a pointing device or via a touch screen.

A clinician or the patient may select or adjust the function 23. In some examples, the user selects or adjusts the ratio to achieve a different profile of stimulation intensity adjustment, e.g., a different degree of aggressiveness of intensity increases. The user may select or adjust function 23 using up and down arrow keys, or via a graphical representation of increasing and decreasing aggressiveness, e.g., a slider-bar. In some examples, a user may program IMD 20 or programmer 30 to automatically select different functions 23 at different times of day or in response to a sensor signal, such as an accelerometer, indicating different levels or activity or different postures, e.g., a more aggressive function during the day or during high activity, and a less aggressive function at night or during low activity.

Figure 8:
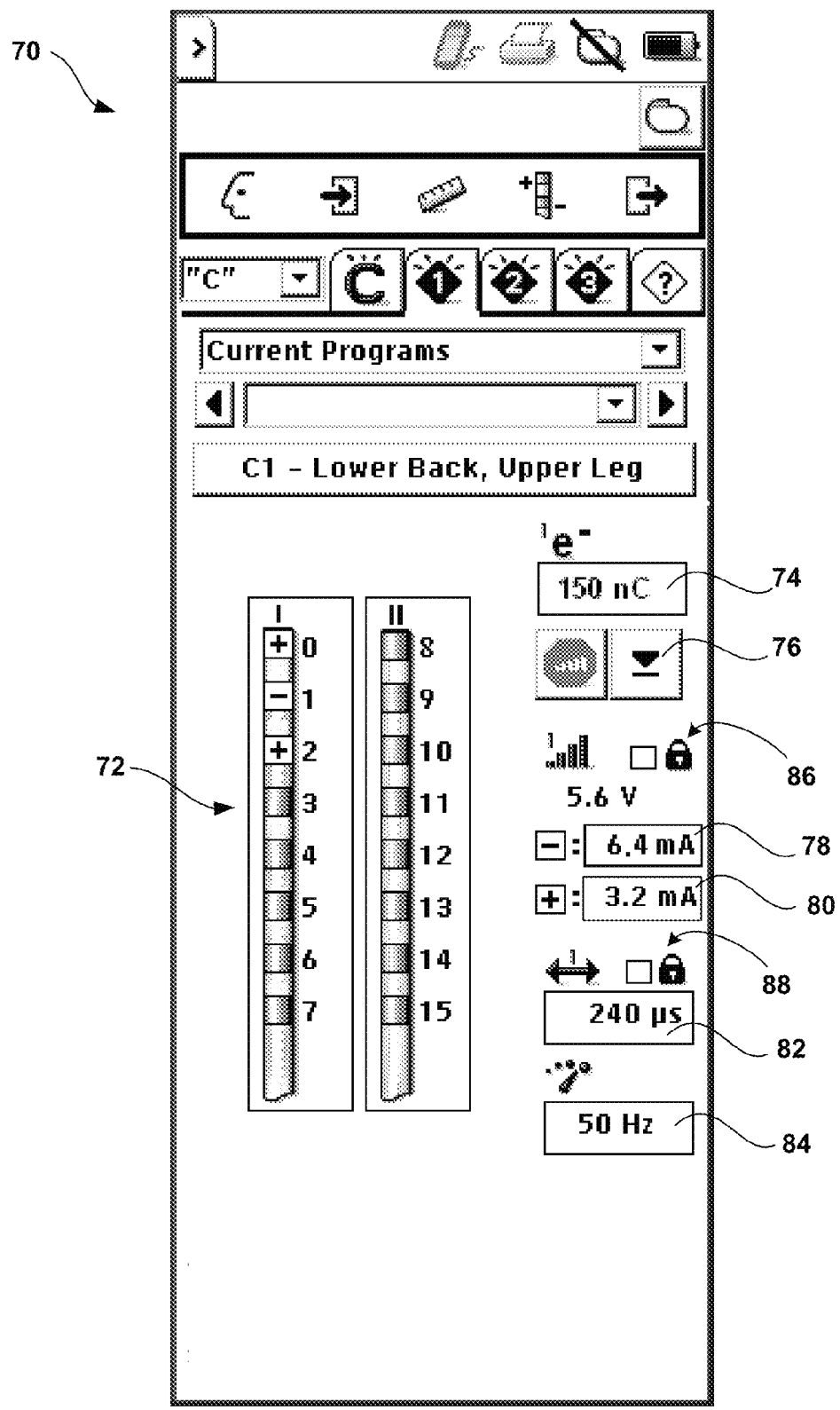
FIG. 8 is a conceptual diagram illustrating an example user interface that facilitates charge-based stimulation intensity programming.

FIG. 8 is a conceptual diagram illustrating an example graphical user interface (GUI) 70 that facilitates charge-based stimulation intensity programming. GUI 70 is presented by user interface 36 of programmer 30 under the direction of processor 32 of programmer 30. As illustrated in FIG. 8, GUI 70 includes a representation 72 of implanted leads and electrodes, which may correspond to leads 16 and electrodes 21. Representation 72 includes indications of which electrodes are active and their polarities.

GUI 70 also includes a displayed electrical charge value 74 for the stimulation delivered by IMD 20, which a user may modify using input media 76. GUI 70 also displays the voltage amplitude, the current amplitude on cathodes 78, the current amplitude on anodes 80, the pulse width 82 and pulse frequency 84 for the stimulation delivered by IMD 20. Frequency 84 is adjustable by the user via user interface 36 of programmer 30. In some examples, one or more of current amplitudes 78 and 80 and pulse width 82 are independently adjustable by the user via user interface 36 of programmer 30, i.e., along with charge 74. In some examples, none of current amplitudes 78 and 80 and pulse width 82 are adjustable by the user via user interface 36 of programmer 30, but are updated as charge 74 is adjusted and displayed as a reference to the user. The voltage amplitude may be determined by measuring the impedances between every anode and cathode and using an equivalent impedance to derive voltage from the current amplitude of the cathodes.

In the illustrated example, GUI 70 also provides input media 86 for receiving a user input to lock pulse amplitude and input media 88 for receiving a user input to lock pulse width. As discussed herein, generally when a user changes electrical charge value 74, IMD 20 and/or programmer 30 modify both pulse amplitude 78, 80 and width 82 to provide the desired charge while maintaining the relationship between pulse amplitude and width defined by function 23. When one of pulse amplitude or pulse width is locked and the user changes charge value 74, IMD 20 and/or programmer 30 modify the unlocked one of pulse amplitude and width to provide the desired charge.

Figure 9:
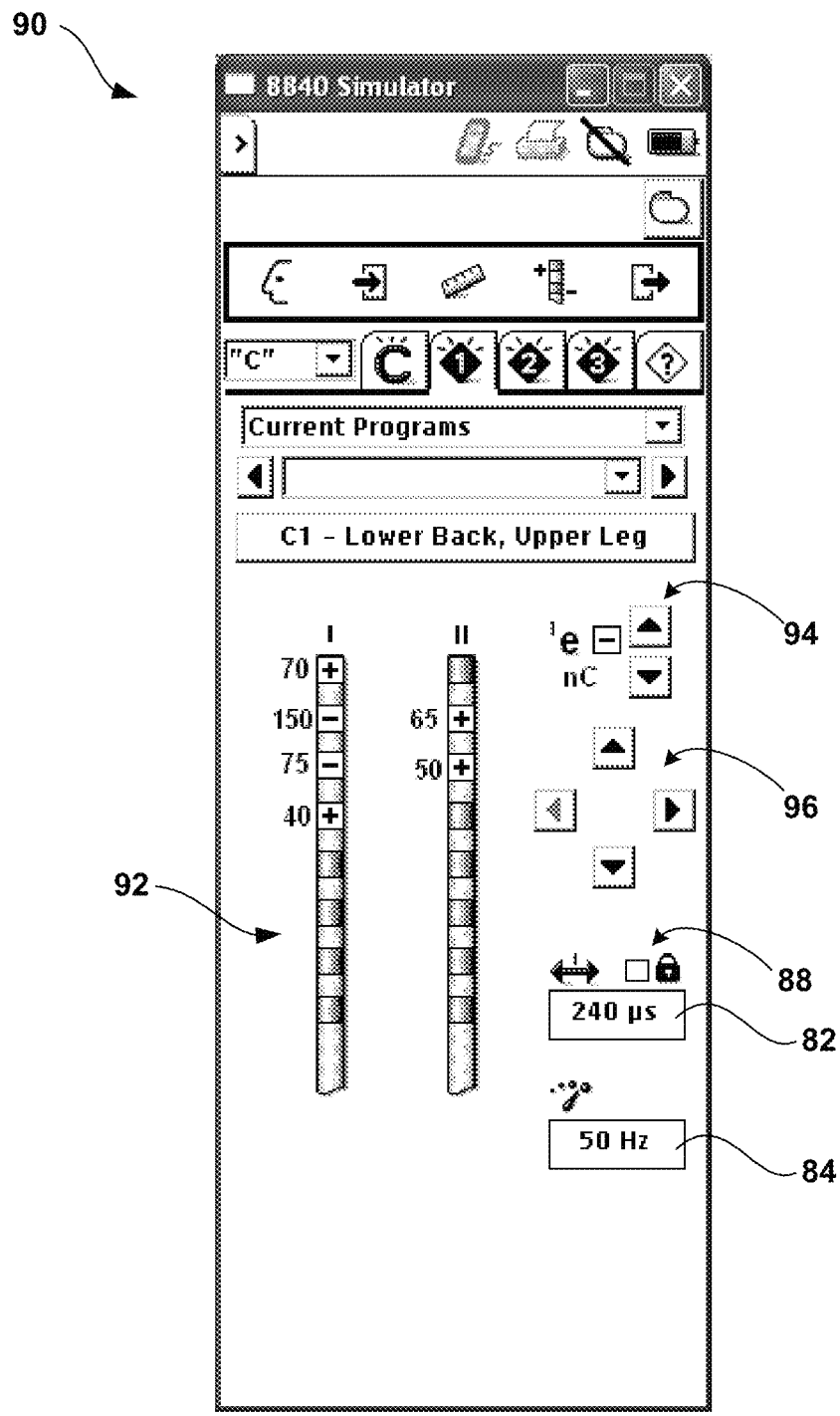
FIG. 9 is a conceptual diagram illustrating another example user interface that facilitates charge-based stimulation intensity programming.

FIG. 9 is a conceptual diagram illustrating another example GUI 90 that facilitates charge-based stimulation intensity programming. GUI 90 includes representation 92 of implanted leads and electrodes. GUI 90 further displays respective charge density values for active electrodes proximate to the representations of the active electrodes. Thus, GUI 90 displays an electrical charge value by displaying charge densities. The charge density for an electrode is a function of the surface area of the electrode and the amount of charge entering/leaving the electrode.

GUI 90 includes input media 94 for receiving user input modifying electrical charge, e.g., the displayed charge densities. GUI 90 also includes input media 96 for directing the charge to different electrodes. Presenting charge density may be particularly beneficial in the context of DBS for safety reasons, e.g., because patient 12 may not perceive harmful stimulation. In some examples, as the user increases the intensity or charge via media 94, or directs or distributes the charge among electrodes using media 96, the user would be able to view in substantially real time what the charge density is on each electrode.

Figure 10:
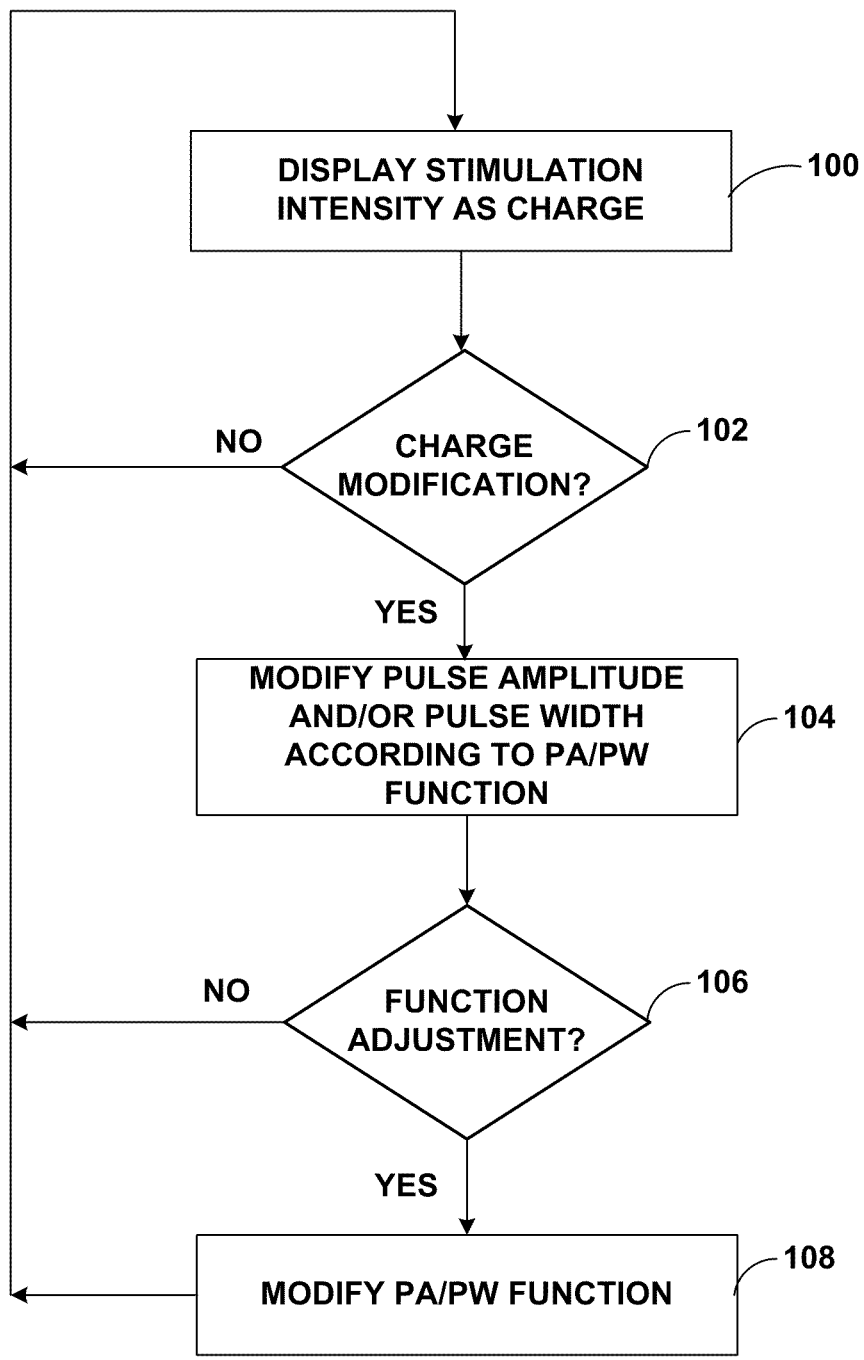
FIG. 10 is a flow diagram illustrating an example technique for charge-based stimulation intensity programming using a function relating pulse amplitude and width.

FIG. 10 is a flow diagram illustrating an example technique for charge-based stimulation intensity programming using a function defining a relationship between pulse amplitude and width. The technique of FIG. 10 is described as being performed by programmer 30, e.g., processor 32. In other examples, IMD 20, e.g., processor 22, or another device may perform some or all of the functions of the example technique of FIG. 10.

Under the control of processor 32, user interface 36 displays stimulation intensity as an electrical charge value (100). Processor 32 determines whether user interface 36 has received a modification of the displayed charge value (102). When a charge modification is received from a user, processor 32 modifies the pulse amplitude and pulse width of stimulation delivered by IMD 20, e.g., by communicating with IMD 20 via communication module 38 (104). Processor 32 modifies the pulse amplitude and width by selecting a combination of pulse amplitude and width that provides the modified charge and also conforms to the pulse amplitude/pulse width function 23 stored in memory 34.

In some examples, processor 32 receives an adjustment to or selection of function 32 from a user via user interface 36 (106). In response to receiving a function 23 selection or adjustment, processor 32 modifies ratio 23 in memory 34 (108). Subsequent modifications of pulse amplitude and width (104) will be in accordance with the modified function 23.

In examples in which charge can be directed or moved amongst electrodes, as discussed above with respect to FIG. 9, processor 32 may respond differently to a request for modified intensity, e.g., a change in the displayed charge, based on whether the electrodes are anodes or cathodes. In the case of cathodes, processor 32 may modify both pulse amplitude and width in accordance with function 23 as described above. In the case of anodes, processor 32 may, in some cases, modify only pulse amplitude.

Figure 11:
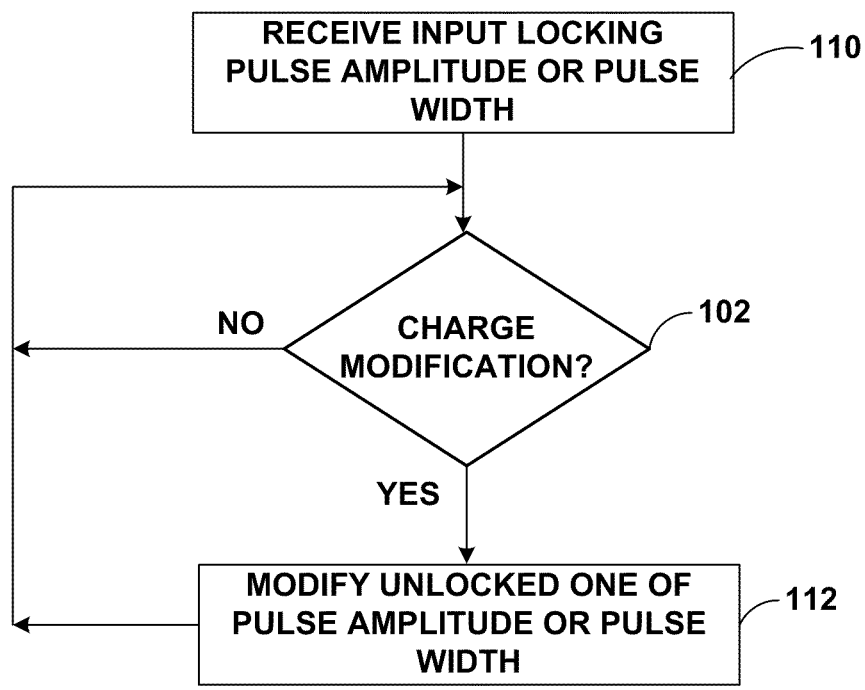
FIG. 11 is a flow diagram illustrating another example technique for charge-based stimulation intensity programming in which one or both of pulse amplitude and pulse width are lockable.

FIG. 11 is a flow diagram illustrating another example technique for charge-based stimulation intensity programming in which one or both of pulse amplitude and pulse width are lockable. The technique of FIG. 11 is described as being performed by programmer 30, e.g., processor 32. In other examples, IMD 20, e.g., processor 22, or another device may perform some or all of the functions of the example technique of FIG. 11.

User interface 36 receives user input locking pulse amplitude or width, e.g., via input medium 86 or 88 (110). Processor 32 then determines whether user interface 36 has received a subsequent modification of the displayed charge value (102). When a charge modification is received from a user, processor 32 modifies the unlocked one of pulse amplitude and pulse width (112).

Processor 32 may modify only one of pulse amplitude or width in other situations. For example, if a user increases charge value 74, but the amplitude is already at its highest setting, the pulse width can be adjusted instead automatically.

Figure 12:
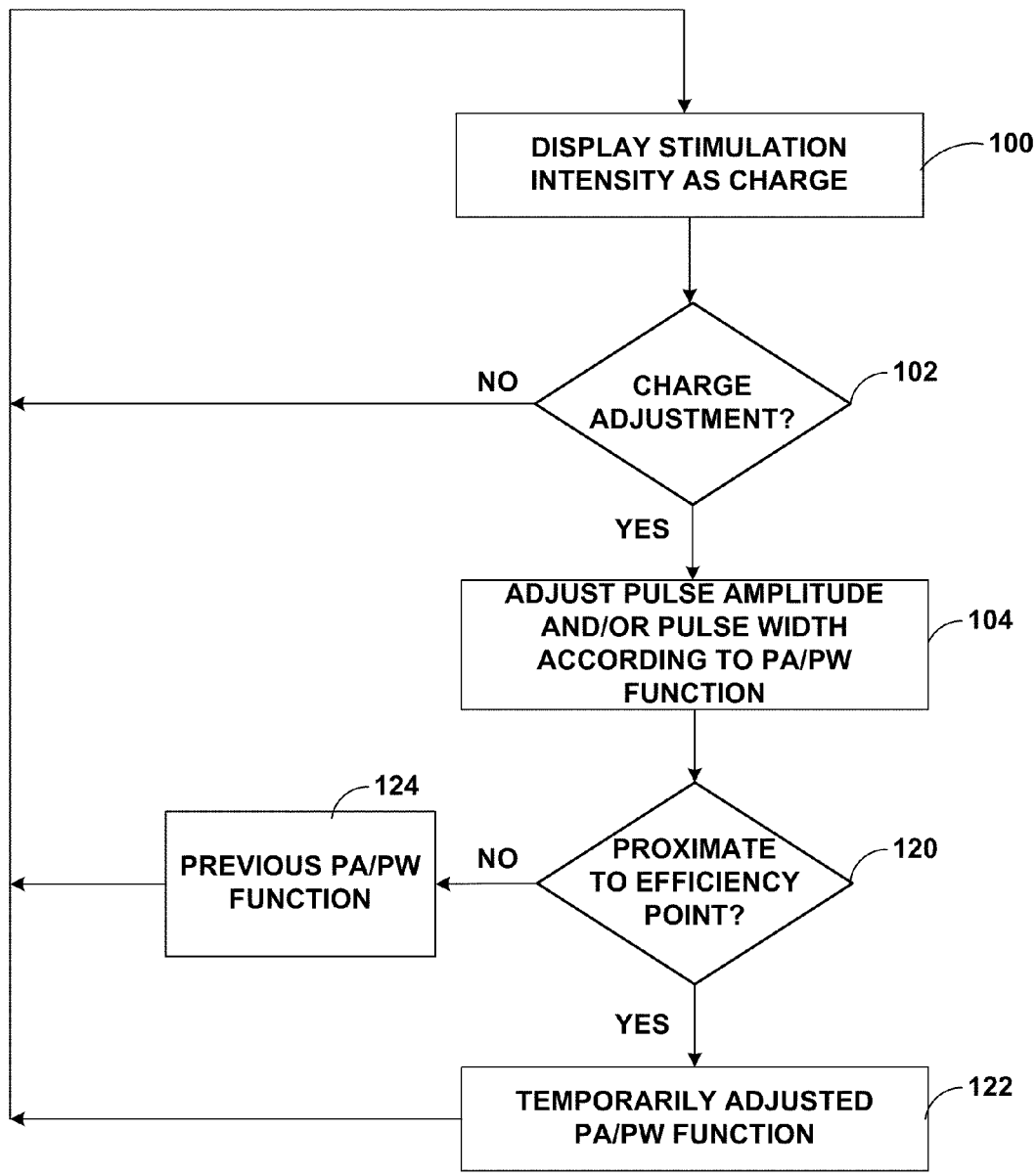
FIG. 12 is a flow diagram illustrating another example technique for charge-based stimulation intensity programming in which a function relating pulse amplitude and width is automatically adjusted based on stimulation efficiency.

FIG. 12 is a flow diagram illustrating another example technique for charge-based stimulation intensity programming in which a ratio between pulse amplitude and width is automatically adjusted based on stimulation efficiency. The technique of FIG. 12 is described as being performed by programmer 30, e.g., processor 32. In other examples, IMD 20, e.g., processor 22, or another device may perform some or all of the functions of the example technique of FIG. 12.

Under the control of processor 32, user interface 36 displays stimulation intensity as an electrical charge value (100). Processor 32 determines whether user interface 36 has received a modification of the displayed charge value (102). When a charge modification is received from a user, processor 32 modifies the pulse amplitude and pulse width of stimulation delivered by IMD 20, e.g., by communicating with IMD 20 via communication module 38 (104). Processor 32 modifies the pulse amplitude and width by selecting a combination of pulse amplitude and width that provides the modified charge and also conforms to the pulse amplitude/pulse width function 23 stored in memory 34.

Processor 32 also determines whether one of pulse amplitude or width is proximate to an efficiency point based on efficiency information 25 (120). For example, processor 32 may determine that pulse amplitude is proximate to a value that would require boosting of the voltage of power source 29 of IMD 20 to provide the required pulse amplitude. If pulse amplitude or width is proximate to an efficiency point, processor 32 automatically and temporarily adjusts function 23 (122). For example, processor 32 may reduce the slope of the function, e.g., ratio of pulse amplitude to width, to increase the number of adjustments before pulse amplitude reaches a value where boosting is required.

Processor 32 may store the adjusted function 23 with the function 23 prior to adjustment, for reversion to the prior function 23 (124) when amplitude or width is no longer proximate to the efficiency point. Modification of pulse amplitude or width 104 will be according to either function, depending on proximity to the efficiency point (120).

Figure 13:
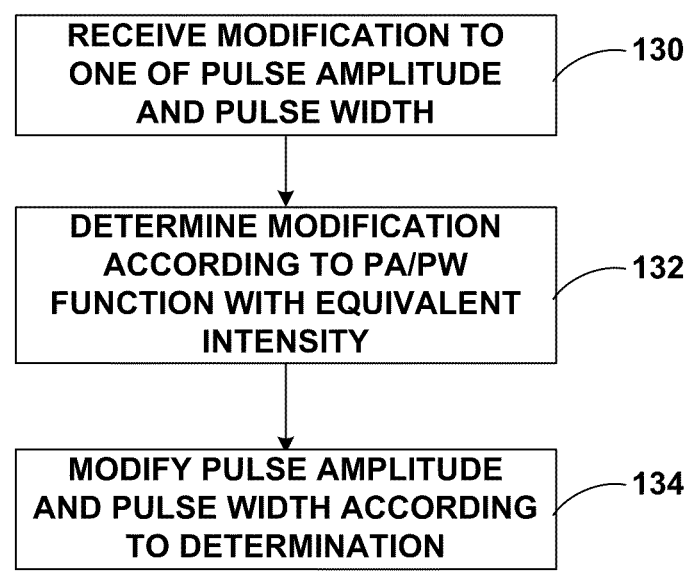
FIG. 13 is a flow diagram illustrating an example technique for charge-based stimulation intensity programming based on receipt of pulse amplitude or pulse width.

FIG. 13 is a flow diagram illustrating an example technique for charge-based stimulation intensity programming based on receipt of pulse amplitude or pulse width. The technique of FIG. 13 is described as being performed by programmer 30, e.g., processor 32. In other examples, IMD 20, e.g., processor 22, or another device may perform some or all of the functions of the example technique of FIG. 13.

According to the illustrated example, user interface 36 receives a modification to one of pulse amplitude or pulse width, e.g., via input media 78, 80, or 82 (130). In response to such a modification, processor 32 determines a modification to both pulse amplitude and pulse width that has equivalent intensity to the user entered modification and maintains ratio 23 between pulse amplitude and width (132). With reference to FIGS. 6A and 6B, for purposes of illustration, the determined pulse amplitude and width pair may be located on a common equal intensity curve 40, 50, 52 with a pulse amplitude and pulse width pair resulting from the user's requested increase in amplitude or width. The determined pulse amplitude and width pair may also be located on the line 60, 62, 64, or curve 66 representing the pulse amplitude and pulse width function 23. Processor 32 modifies pulse amplitude and width to the determined pair that maintains function 23 (134).

Figure 14:
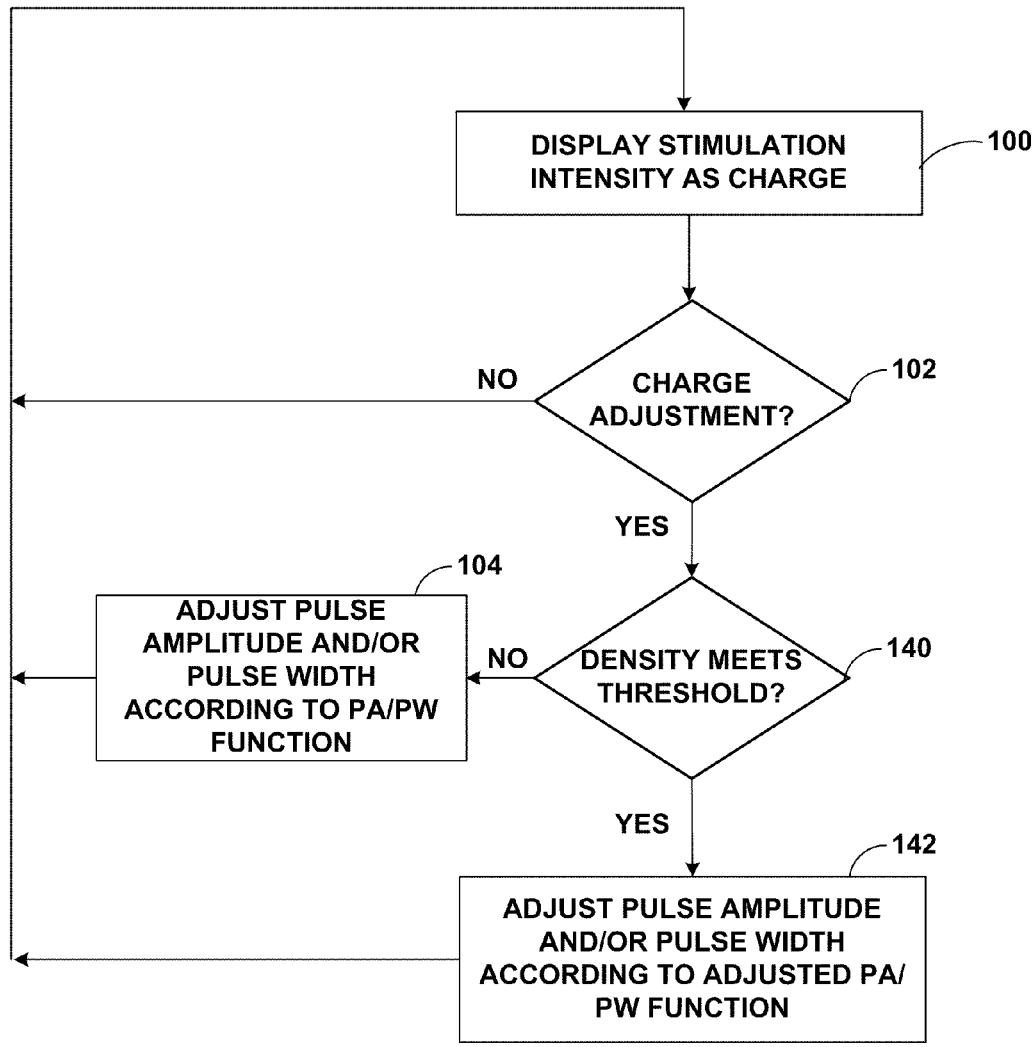
FIG. 14 is a flow diagram illustrating an example technique for responding to user requests for increased charge when the charge density on an electrode meets a threshold value.

FIG. 14 is a flow diagram illustrating an example technique for responding to user requests for increased charge when the charge density on an electrode meets a threshold value. The technique of FIG. 14 is described as being performed by programmer 30, e.g., processor 32. In other examples, IMD 20, e.g., processor 22, or another device may perform some or all of the functions of the example technique of FIG. 14.

Under the control of processor 32, user interface 36 displays stimulation intensity as an electrical charge value (100). Processor 32 determines whether user interface 36 has received a modification of the displayed charge value (102). When a charge modification is received from a user, processor 32 determines whether the charge density of one or more of electrodes 21 exceeds a predetermined threshold value, which may be a safety factor below a charge density value at which tissue damage is possible (140). The threshold value may be stored in memory 34 of programmer 30, or memory 24 of IMD 20. Processor 32 may determine the charge densities of electrodes 21 based on information specifying the surface area of electrodes 21 stored in memory 34 or 24, as well as a determination of the charge provided to each of the electrodes according to the current parameters of the neurostimulation delivered to the patient.

So long as the charge density on electrodes 21 has not met the threshold, processor 32 adjusts the pulse amplitude and/or pulse width according to the function 23 (104). If the density on one or more of the electrodes 21 meets the threshold value, processor adjusts function 23 to alleviate the charge density, and adjusts pulse amplitude and/or pulse width according to the adjusted function 23 (142). The adjusted function 23 may specify that further requests for increased stimulation intensity or charge are responded to by increasing pulse amplitude and decreasing pulse width, such that intensity is increased without increasing charge or charge density. User requests for decreased stimulation intensity or charge may be responded to be decreasing amplitude and increasing pulse width. Processor 32 may allow a user to titrate along such an adjusted function until the point of departure from the original function is met and/or the charge density no longer exceeds the threshold value.

Various examples have been described. One of ordinary skill in the art will understand that various modifications may be made to the described examples without departing from the scope of the claims. For example, although described primarily with respect to examples in which an electrical charge value is displayed to a user, in other examples a user may control the charge provided by the stimulation without the display of a charge value or adjustment of the displayed charge value. In other examples, user input that controls the charge provided by electrical stimulation may include manipulation of up or down arrows, whether physical or graphical, a slider-bar, or the like.

Furthermore, some examples need not include a computing or programming device to receive user input. In some examples, the medical device may provide a user interface for receiving user input, such as a sensor to detect the presence of a magnet, which may be controlled by a user, in the case of an implantable medical device. These and other examples are within the scope of the following claims.

The invention claimed is:
1. A method comprising:
  storing a predetermined function specifying a relationship between pulse amplitude and pulse width within a memory;
  receiving input from a user modifying an electrical charge value of neurostimulation therapy delivered by a medi- cal device, wherein the input from the user indicates the modification with regard to electrical charge value;

modifying a pulse amplitude and a pulse width of the neurostimulation therapy delivered by the medical device according to the function and based on the modification to the charge value; and controlling the delivery of the neurostimulation therapy to the patient according to the modified pulse amplitude and the modified pulse width, wherein the neurostimulation therapy comprises a plurality of electrical stimulation pulses, and wherein the modified pulse amplitude and the modified pulse width are defined for each of the plurality of electrical stimulation pulses.

2. The method of claim 1, wherein the function is programmable by the user.

3. The method of claim 1, further comprising:
receiving user input locking one of the pulse amplitude or the pulse width of the neurostimulation therapy;
receiving subsequent input modifying the electrical charge value; and
modifying an unlocked one of the pulse amplitude or the pulse width of the neurostimulation therapy based on the subsequent modification to the charge value.

4. The method of claim 1, further comprising:
determining that at least one of the pulse amplitude or the pulse width of the neurostimulation is proximate to a stimulation efficiency point; and
automatically adjusting the function based on the determination.

5. The method of claim 4, wherein determining that the at least one of the pulse amplitude or the pulse width is proximate to a stimulation efficiency point comprises determining that the pulse amplitude is proximate an amplitude for which boosting a voltage of a power source of the medical device is required, and automatically adjusting the function comprises automatically decreasing a slope of the function based on the determination.

6. The method of claim 4, wherein automatically adjusting the function comprises temporarily adjusting the function.

7. The method of claim 1, further comprising displaying the electrical charge value to the user via a user interface, wherein receiving input modifying the electrical charge value comprises receiving user-inputted modifications to the displayed electrical charge value via the user interface.

8. The method of claim 7, wherein displaying an electrical charge value comprises:
displaying, via the user interface, a representation of a plurality of electrodes implanted within the patient; and
displaying, via the user interface, respective charge density values proximate to the electrodes.

9. The method of claim 8,
wherein receiving user-inputted modifications to the displayed electrical charge values comprises receiving user input adjusting relative charge densities of the electrodes, and
wherein modifying the pulse amplitude and the pulse width of the stimulation comprises modifying the pulse amplitude and pulse width of stimulation delivered via cathodes of the electrodes according to the function based on modifications to charge densities of the cathodes, and modifying the pulse amplitude of stimulation delivered via anodes of the electrodes without modifying the pulse width based on modifications to charge densities of the anodes.

10. The method of claim 7, further comprising displaying, via the user interface, at least one of the amplitude value or the pulse width value in addition to the electrical charge value.

11. The method of claim 7, wherein displaying, via the user interface, the electrical charge value comprises displaying the electrical charge value via a display of the user interface, and receiving the user-inputted modifications to the displayed electrical charge value comprises receiving the user-inputted modifications via the display.

12. The method of claim 1, further comprising:
receiving user-inputted modifications to one of the pulse amplitude or the pulse width;
determining a modification to both of the pulse amplitude and the pulse width according to the function with equivalent intensity to the user-inputted modification to the one of the pulse amplitude or pulse width; and
modifying the pulse amplitude and the pulse width according to the determination.

13. The method of claim 1, further comprising:
determining that a charge density for an electrode through which the medical device delivers the neurostimulation therapy meets a predetermined threshold value;
receiving user input increasing the charge value subsequent to the determination that the charge density meets the predetermined threshold value; and
increasing the pulse amplitude and decreasing the pulse width in response to the subsequent user input.

14. The method of claim 1, wherein the neurostimulation therapy comprises spinal cord stimulation or deep brain stimulation.

15. The method of claim 1, wherein receiving input from a user comprises receiving the input via a user interface of a programming device that communicates with the medical device.

16. A system comprising:
a memory configured to store a predetermined function specifying a relationship between pulse amplitude and pulse width;
a medical device configured to deliver neurostimulation therapy including a plurality of electrical stimulation pulses to a patient;
a user interface configured to receive input from a user modifying an electrical charge value of the neurostimulation therapy, wherein the input from the user indicates the modification with regard to electrical charge value; and
at least one processor configured to modify a pulse amplitude and a pulse width for each of the plurality of electrical stimulation pulses delivered by the medical device according to the function and based on the modification to the charge value such that the modified pulse amplitude and the modified pulse width are defined for each of the plurality of electrical stimulation pulses, and control the delivery of the plurality of electrical stimulation pulses to the patient via the medical device according to the modified pulse amplitude and the modified pulse width for each of the plurality of electrical stimulation pulses.

17. The system of claim 16, wherein the function is programmable by the user via the user interface.

18. The system of claim 16, wherein the user interface receives user input locking one of the pulse amplitude or the pulse width of the neurostimulation therapy, and subsequent input modifying the electrical charge value, and the at least one processor modifies an unlocked one of the pulse amplitude or the pulse width of the neurostimulation therapy delivered by the medical device based on the subsequent modifications to the charge value.

19. The system of claim 16, wherein the at least one processor determines that at least one of the pulse amplitude or the pulse width of the neurostimulation therapy is proximate to a stimulation efficiency point, and automatically adjusts the function based on the determination.

20. The system of claim 19, wherein the at least one processor determines that the at least one of the pulse amplitude or the pulse width of the neurostimulation therapy is proximate to a stimulation efficiency point by at least determining that the pulse amplitude is proximate an amplitude for which boosting a voltage of a power source of the medical device is required, and wherein the processor automatically adjusts the function based on the determination by at least automatically decreasing a slope of the function based on the determination.

21. The system of claim 16,
wherein the user interface displays the electrical charge value to a user, and receives user-inputted modifications to the displayed electrical charge value, and
wherein the at least one processor modifies the pulse amplitude and the pulse width for each of the plurality of electrical stimulation pulses delivered by the medical device according to the function and based on the modifications to the displayed charge value for each of the plurality of electrical stimulation pulses.

22. The system of claim 21, wherein the user interface displays a representation of a plurality of electrodes implanted within the patient, and displays respective charge density values proximate to the electrodes.

23. The system of claim 21, wherein the user interface comprises a display and receives the user-inputted modifications via the display.

24. The system of claim 16,
wherein the processor determines that a charge density for an electrode through which the medical device delivers the neurostimulation therapy meets a predetermined threshold value,
wherein the user interface receives user input increasing the charge value subsequent to the determination that the charge density meets the predetermined threshold value, and
wherein the at least one processor controls the medical device to increase the pulse amplitude and decrease the pulse width of the neurostimulation therapy in response to the subsequent user input.

25. The system of claim 16, further comprising an external programming device that comprises the user interface, the memory and the at least one processor, wherein the medical device comprises an implantable medical device, and the programming device communicates with the implantable medical device.

26. A system comprising:
means for storing a predetermined function specifying a relationship between pulse amplitude and pulse width;
means for receiving input from a user modifying an electrical charge value of neurostimulation therapy comprising a plurality of electrical stimulation pulses delivered by a medical device, wherein the input from the user indicates the modification with regard to electrical charge value;
means for modifying a pulse amplitude and a pulse width for each of the plurality of electrical stimulation pulses delivered by the medical device according to the function and based on the modification to the charge value such that the modified pulse amplitude and the modified pulse width are defined for each of the plurality of electrical stimulation pulses; and
means for controlling the delivery of the plurality of electrical stimulation pulses to the patient according to the modified pulse amplitude and the modified pulse width for each of the plurality of electrical stimulation pulses.

27. The system of claim 26, further comprising means for receiving selection of the function from a user.

28. A non-transitory computer-readable storage medium comprising instructions that cause a programmable processor to:
retrieve a predetermined function defining a relationship between pulse amplitude and pulse width from a memory;
receive input from a user modifying an electrical charge value of neurostimulation therapy delivered by a medical device, wherein the input from the user indicates the modification with regard to electrical charge value;
modify a pulse amplitude and a pulse width of the neurostimulation therapy delivered by the medical device according to the function and based on the modification to the charge value; and
control the delivery of the neurostimulation therapy to the patient according to the modified pulse amplitude and the modified pulse width,
wherein the neurostimulation therapy comprises a plurality of electrical stimulation pulses, and
wherein the modified pulse amplitude and the modified pulse width are defined for each of the plurality of electrical stimulation pulses.

29. The method of claim 1, wherein the plurality of electrical stimulation pulses comprise a first electrical stimulation pulse and a second electrical stimulation pulse, wherein the modified pulse amplitude and the modified pulse width are defined for both the first electrical stimulation pulse and the second electrical stimulation pulse.

30. The system of claim 16, wherein the plurality of electrical stimulation pulses comprise a first electrical stimulation pulse and a second electrical stimulation pulse, wherein the modified pulse amplitude and the modified pulse width are defined for both the first electrical stimulation pulse and the second electrical stimulation pulse.

* * * * *